United States Patent
Kawahara (10) Patent No.: US 7,375,818 B2
(45) Date of Patent: May 20, 2008

(54) OPTICAL TOMOGRAPHY SYSTEM

(75) Inventor: Karin Kawahara, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 53 days.

(21) Appl. No.: 11/540,683

(22) Filed: Oct. 2, 2006

(65) Prior Publication Data
US 2007/0076222 A1    Apr. 5, 2007

(30) Foreign Application Priority Data
Sep. 30, 2005  (JP)  ............. 2005-289119

(51) Int. Cl.
*G01B 9/02*  (2006.01)
(52) U.S. Cl. .................. 356/477; 356/479
(58) Field of Classification Search ......... 356/477, 356/479, 497; 250/227.19, 227.27
See application file for complete search history.

(56) References Cited

U.S. PATENT DOCUMENTS 5,565,986 A    10/1996  Knüttel
2006/0055936 A1*  3/2006  Yun et al. ............ 356/479
2006/0256348 A1   11/2006  Toida et al.
2007/0002327 A1*  1/2007  Zhou et al. ............ 356/456

FOREIGN PATENT DOCUMENTS

| EP | 1 704 814 | 9/2006 |
| JP | 10-332329 | 12/1998 |
| JP | 2003-172690 A | 6/2003 |
| WO | WO 2005/001401 | 1/2005 |

OTHER PUBLICATIONS

R. Huber, et al., "Fourier Domain Mode Locked Lasers for OCT Imaging at up to 290 kHz Sweep Rates," Optical Coherence Tomography and Coherence Techniques II, edited by Wolfgang Drexler, SPIE-OSA Biomedical Optics, SPIE vol. 5861, 2005. pp. 58611B-1-B-6.

* cited by examiner

*Primary Examiner*—Tarifur Chowdhury
*Assistant Examiner*—Jonathon D Cook
(74) *Attorney, Agent, or Firm*—Sughrue Mion, PLLC (57) ABSTRACT

In an optical tomography system for obtaining a tomographic image of an object to be measured by detecting interference light of the reflected light and the reference light, a controller switches between a first detecting mode in which the interference light is detected at a first wavelength resolution and a second detecting mode in which the interference light is detected at a second wavelength resolution higher than the first wavelength resolution.

17 Claims, 4 Drawing Sheets

OPTICAL TOMOGRAPHY SYSTEM

BACKGROUND OF THE INVENTION

1. Field of the Invention

This invention relates to an optical tomography system for obtaining an optical tomographic image by measurement of OCT (optical coherence tomography).

2. Description of the Related Art

As a system for obtaining a tomographic image of an object of measurement in a body cavity, there has been known an ultrasonic tomography system. In addition to such an ultrasonic tomography system, there has been proposed an optical tomography system where an optical tomographic image is obtained on the basis of an interference of light by low coherence light. See, for instance, Japanese Unexamined Patent Publication No. 2003-172690. In the system disclosed in Japanese Unexamined Patent Publication No. 2003-172690, an optical tomographic image is obtained by measuring TD-OCT (time domain OCT) and the measuring light is guided into the body cavity by inserting a probe into the body cavity from the forceps port of an endoscope by way of a forceps channel.

More specifically, low coherence light emitted from a light source is divided into measuring light and reference light and the measuring light is projected onto the object of measurement, while the reflected light from the object of measurement is led to a multiplexing means. The reference light is led to the multiplexing means after its optical path length is changed. By the multiplexing means, the reflected light and the reference light are superposed one on another, and interference light due to the superposition is detected by, for instance, heterodyne detection. In the TD-OCT measurement, a phenomenon that interference light is detected when the optical path of the measuring light conforms to the optical path of the reference light in length is used and the measuring position (the depth of measurement) in the object is changed by changing the optical path length of the reference light.

When measuring the OCT by inserting a probe into a body cavity, the probe is mounted on the system body to be demountable since disinfection, cleaning and the like of the probe after use are necessary. That is, a plurality of probes are prepared for one optical tomography system and the probes are changed by the measurement. However there is an individual difference in the length of the optical fiber due to the manufacturing errors and the like, and the optical path length of the measuring light can change each time the probe is changed. Accordingly, in Japanese Unexamined Patent Publication No. 2003-172690, on the basis of the reflected light from the inner surface of a tube (sheath) covering an optical fiber of the probe, the optical path length of the reference light is adjusted to conform to the optical path length of the measuring light.

Whereas, as a system for rapidly obtaining a tomographic image without changing the optical path length of the reference light such as disclosed above, there has been proposed an SS-OCT (swept source OCT) system where interference light is detected while the frequency of the light emitted from the light source is changed with time. In the SS-OCT system, an interferogram interference intensity signal is obtained without changing the optical path length by sweeping the frequency of the laser beam emitted from the light source to cause the reflected light and the reference light to interfere with each other by the use of a Michelson interferometer. Then a tomographic image is generated by carrying out a Fourier analysis on the interferogram signal in the region of an optical frequency.

SUMMARY OF THE INVENTION

In the SS-OCT measurement, it is not necessary to conform the optical path length of the measuring light to that of the reference light since information on the reflection in positions in the direction of depth can be obtained by carrying out frequency-analysis. However, there arises a problem that when the optical path length difference becomes large, the spatial frequency of the interference signal is enlarged and the S/N of the detected interference signal deteriorates due to limitation on the sampling time of the photodiodes such as CCDs for detecting the interference light. Accordingly, also in the SS-OCT measurement, it is still necessary to adjust the optical path length so that the optical path length of the measuring light substantially conforms to that of the reference light and the measurement initiating position is adjusted to a position in which the object is included in the measurable range.

The measurable range (measuring depth) over which a tomographic image is obtainable by the SS-OCT measurement is reverse proportional to the fluctuation width of the wavelength per unit time of the light source, and the resolution in the direction of the optical axis when a tomographic image is obtained increases as the fluctuation width of the wavelength per unit time of the light source becomes wider. That is, the measurable range (measuring depth) becomes narrow when a tomographic image is obtained at a high resolution in a predetermined time. Accordingly, it takes a long time to bring the optical path length difference between the measuring light and the reference light to the measurable range since the measurable range (measuring depth) is narrow to obtain a tomographic image in order to adjust the measurement initiating position in an SS-OCT system for obtaining a high resolution tomographic image. Similarly, there is a problem that when layer structure such as of the stomach wall is to be observed, the tomographic image thereof cannot be obtained due to the measurable range (measuring depth).

In view of the foregoing observations and description, the primary object of the present invention is to provide an optical tomography system where a tomographic information is obtained by projecting the measuring light onto the object while sweeping at the wavelength of the measuring light and carrying out frequency-analysis on the interference light at that time which can be switched in its measurable range (measuring depth) according to the application and is improved in convenience.

In accordance with the present invention, there is provided an optical tomography system for obtaining a tomographic image of an object to be measured comprising a light source unit which emits light while sweeping the wavelength thereof at predetermined periods, a light dividing means which divides the light emitted from the light source unit into measuring light and reference light, a multiplexing means which multiplexes the reflected light from the object when the measuring light divided by the light dividing means is projected onto the object and the reference light, an interference light detecting means which detects interference light of the reflected light and the reference light which have been multiplexed by the multiplexing means, and a tomographic information obtaining means which obtains a tomographic information of the object by carrying out frequency-analysis on the interference light detected by the interference light detecting means, a detecting mode control means which switches between a first detecting mode in which the interference light is detected at a first wavelength resolution and a second detecting mode in which the interference light is detected at a second wavelength resolution higher than the first wavelength resolution being provided.

Since the wavelength is an inverse of the frequency, the expression "a first detecting mode in which the interference light is detected at a first wavelength resolution and a second detecting mode in which the interference light is detected at a second wavelength resolution higher than the first wavelength resolution" can be expressed in other words "a first detecting mode in which the interference light is detected at a first frequency resolution and a second detecting mode in which the interference light is detected at a second frequency resolution higher than the first frequency resolution". Similarly, the light source unit 10 may be expressed in other words "a light source unit which emits light while sweeping the frequency thereof at predetermined periods."

Expression "the reflected light from the object when the measuring light is projected onto the object" means light reflected by the object or light scattered by the object.

The detecting mode control means may increase the wavelength resolution by controlling the light source unit so that the fluctuation width of the wavelength per unit time of the light when the wavelength is swept is smaller in the second detecting mode than in the first detecting mode.

The light source unit may be any so long as it emits light while sweeping the wavelength (frequency) thereof at predetermined periods. For example, various wavelength tunable lasers may be employed as the light source unit.

Further, the detecting mode control means may increase the wavelength resolution by controlling the interference light detecting means so that the sampling frequency is higher in the second detecting mode than in the first detecting mode.

The first detecting mode is an image obtaining mode for obtaining a tomographic image of the object and the second detecting mode is a measurement initiating position adjusting mode in which the position in the direction of depth of the object in which tomographic image signal is to be obtained is adjusted.

An optical path length adjusting means which adjusts the optical path length of the measuring light or the reference light may be provided.

In an optical tomography system for obtaining a tomographic image of an object to be measured comprising a light source unit which emits light while sweeping the wavelength thereof at predetermined periods, a light dividing means which divides the light emitted from the light source unit into measuring light and reference light, a multiplexing means which multiplexes the reflected light from the object when the measuring light divided by the light dividing means is projected onto the object and the reference light, an interference light detecting means which detects interference light of the reflected light and the reference light which have been multiplexed by the multiplexing means, and a tomographic information obtaining means which obtains a tomographic information of the object by carrying out frequency-analysis on the interference light detected by the interference light detecting means, since the measurable range (measuring depth) becomes larger when the wavelength resolution upon detection of the interference light is high and becomes smaller when the wavelength resolution upon detection of the interference light is low, when a first detecting mode in which the interference light is detected at a first wavelength resolution and a second detecting mode in which the interference light is detected at a second wavelength resolution higher than the first wavelength resolution can be switched, the user can switch the measurable range (measuring depth) according to the application and the convenience of the optical tomography system can be improved.

When the wavelength resolution in the second detecting mode is increased by controlling the light source unit so that the fluctuation width of the wavelength per unit time of the light when the wavelength is swept is smaller in the second detecting mode than in the first detecting mode, the measurable range (measuring depth) can be easily switched.

When the wavelength resolution in the second detecting mode is increased by controlling the interference light detecting means so that the sampling frequency is higher in the second detecting mode than in the first detecting mode, the measurable range (measuring depth) can be switched without adding to the time for obtaining a tomographic image.

When the first detecting mode is an image obtaining mode for obtaining a tomographic image of the object and the second detecting mode is a measurement initiating position adjusting mode in which the position in the direction of depth of the object in which tomographic image signal is to be obtained is adjusted, since the wavelength resolution can be increased in the measurement initiating position adjusting mode so that the measurable range (measuring depth) is broadened and the object can be easily found, the object can be apt to be obtained as a tomographic image in the measurement initiating position adjusting mode and the measurement initiating position can be efficiently adjusted.

DESCRIPTION OF THE PREFERRED EMBODIMENTS

Figure 1:
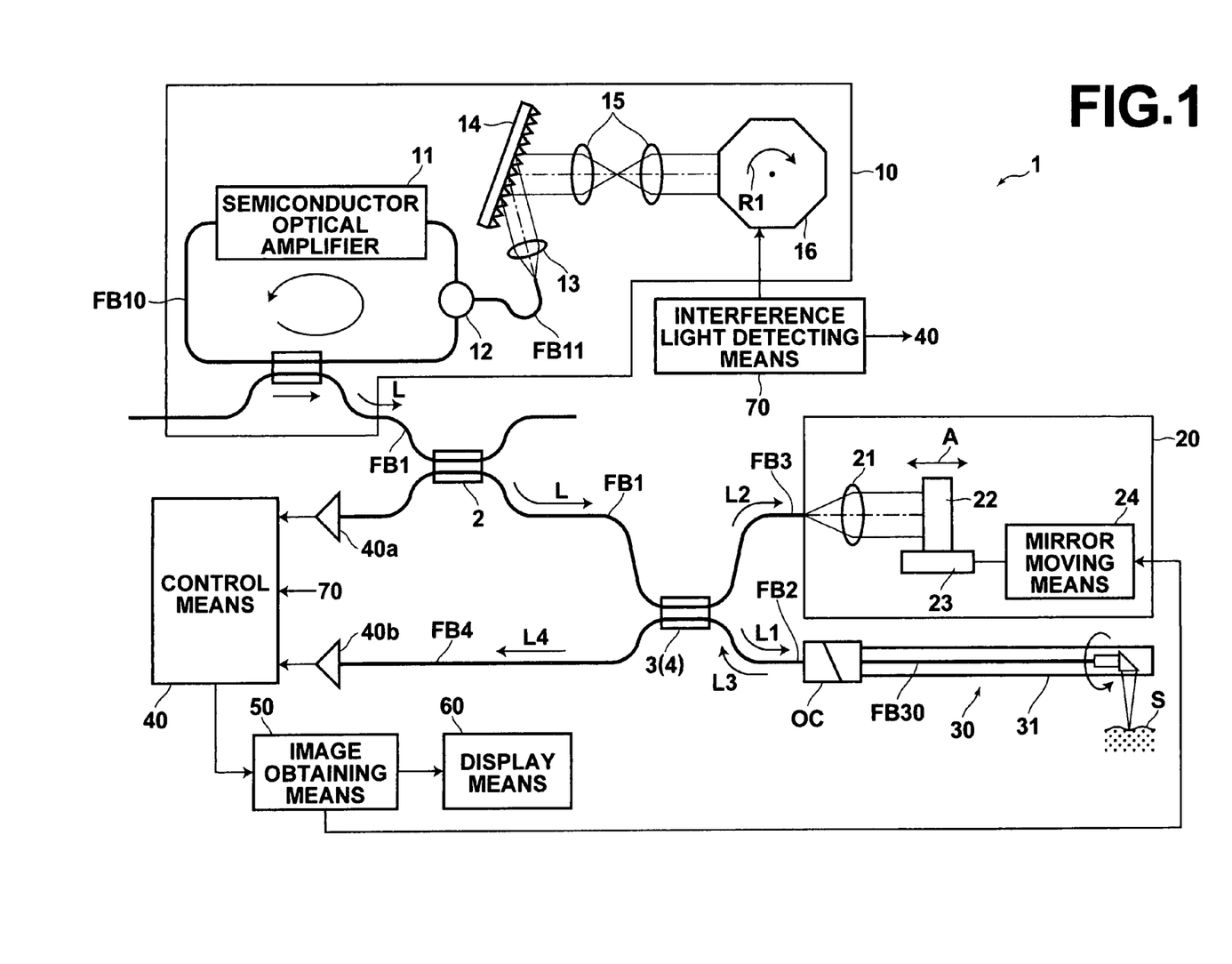
FIG. 1 is a schematic diagram showing an optical tomography system in accordance with a preferred embodiment of the present invention.

Embodiments of the optical tomography system of the present invention will be described in detail with reference to the drawings, hereinbelow. FIG. 1 is a schematic diagram that illustrates an optical tomography system in accordance with a preferred embodiment of the present invention. The optical tomography system 1 of this embodiment is for obtaining a tomographic image of an object of measurement such as a living tissue or a cell in a body cavity by measuring the SS-OCT. The optical tomography apparatus 1 of this embodiment comprises: a light source unit 10 for emitting a laser beam L; a light dividing means 3 for dividing the laser beam L emitted from the light source unit 10 into a measuring light beam L1 and a reference light beam L2; an optical path length adjusting means 20 for adjusting the optical path length of the reference light beam L2 divided by the light dividing means 3; a probe 30 which guides to the object S to be measured the measuring light beam L1 divided by the light dividing means 3; a multiplexing means 4 for multiplexing a reflected light beam L3 from the object S when the measuring light beam L1 is irradiated onto the object S from the probe 30, and the reference light beam L2; an interference light detecting means 40 for detecting interference light beam L4 of the reflected light beam L3 and the reference light beam L2 which have been multiplexed and an image obtaining means 50 which obtains a tomographic image of the object S by carrying out frequency-analysis on the interference light beam L4 detected by the interference light detecting means 40.

The light source unit 10 emits the laser beam L while sweeping the frequency at a constant period and comprises, for instance, a synchronized semiconductor laser. Specifically, the light source unit 10 comprises: a semiconductor optical amplifier 11 (semiconductor gain medium); and an optical fiber FB10 and the optical fiber FB10 is connected to both ends of the semiconductor optical amplifier 11. The semiconductor optical amplifier 11 functions to emit weak release light into a first end of the optical fiber FB10, when a drive current is injected thereinto, and to amplify the light that enters it from a second end of the optical fiber FB10. When the drive current is supplied to the semiconductor optical amplifier 11, a pulse-like laser light beam L is emitted to an optical fiber FB1 from an optical resonator formed by the semiconductor optical amplifier 11 and the optical fiber FB10.

Further, an optical divider 12 is linked to the optical fiber FB10, and a portion of the light beam that propagates within the optical fiber FB10 is emitted into an optical fiber FB11 from the optical divider 12. The Light beam, which is emitted from the optical fiber FB11, passes through a collimator lens 13, a diffraction grating 14, and an optical system 15, to be reflected by a rotating polygon mirror 16. The light beam reflected by the rotating polygon mirror 16 reenters the optical fiber FB11 by way of the optical system 15, the diffraction grating 14, and the collimator lens 13.

Figure 2:
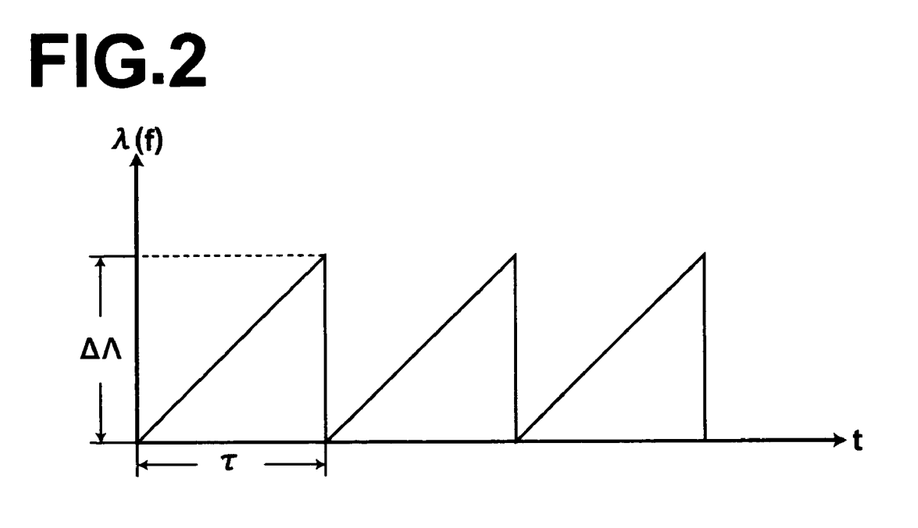
FIG. 2 is a view for illustrating an example of the wavelength fluctuation of a laser beam output from the light source unit shown in FIG. 1 in the image obtaining mode.

The rotating polygon mirror 16 rotates in the direction indicated by arrow R1, to vary the angle of each reflective surface thereof with respect to the optical axis of the optical system 15. Thereby, only a light beam having a specific frequency, from among the light spectrally split by the diffraction grating 14, is returned to the optical fiber FB11. The frequency of the light beam that reenters the optical fiber FB11 is determined by the angle formed by the optical axis of the optical system 15 and the reflective surface of the rotating polygon mirror 16. Light beam of the specific wavelength band entering the optical fiber FB11 enters the optical fiber FB10 from the optical divider 12, and, as a result, a laser beam L of a specific wavelength band is emitted to the optical fiber FB1. Accordingly, when the rotating polygon mirror 16 rotates in the direction indicated by arrow R1 at a constant speed, the wavelength of the light beam which reenters the optical fiber FB11 is swept at a period as shown in FIG. 2. As a result, a laser beam L the wavelength of which has been swept at constant periods is emitted from the light source unit 10 to the optical fiber FB1.

The light dividing means 3 of FIG. 1 comprises, for instance, a 2×2 fiber optic coupler and divides the light beam L led thereto by way of the optical fiber FB1 from the light source unit 10 into the measuring light beam L1 and the reference light beam L2. The light dividing means 3 is optically connected to two optical fibers FB2 and FB3, and the measuring light beam L1 is propagated through the optical fiber FB2 while the reference light beam L2 is propagated through the optical fiber FB3. In FIG. 1, the light dividing means 3 also functions as the multiplexing means 4.

The probe 30 is optically connected to the optical fiber FB2 and the measuring light beam L1 is guided to the probe 30 from the optical fiber FB2. The probe 30 is inserted into a body cavity, for instance, through a forceps port by way of a forceps channel and is removably mounted on the optical fiber FB2 by an optical connector OC.

The optical path length adjusting means 20 is disposed on the side of the optical fiber FB3 radiating the reference light beam L2. The optical path length adjusting means 20 changes the optical path length of the reference light beam L2 in order to adjust the measurement initiation position with respect to the object S and comprises a collimator lens 21 and a reflecting mirror 22. The reference light beam L2 radiated from the optical fiber FB3 passes through the collimator lens 21 and is reflected by the reflecting mirror 22 and reenters the optical fiber FB3 by way of the collimator lens 21.

The reflecting mirror 22 is disposed on a movable stage 23 which is moved in the direction of arrow A by a mirror moving means 24. In response to movement of the movable stage 23 in the direction of arrow A, the optical path length of the reference light L2 is changed.

The multiplexing means 4 comprises a 2×2 fiber optic coupler, and multiplexes the reference light beam L2 which has been changed in its optical path length and its frequency by the optical path length adjusting means 20 and the reflected light from the object S to emit the multiplexed light beam toward an interference light detecting means 40 by way of an optical fiber FB4.

The interference light detecting means 40 detects interference light L4 of the reflected light beam L3 and the reference light beam L2 which have been multiplexed by the multiplexing means 4 at a predetermined sampling frequency and comprises InGaAs series photodetectors 41a and 41b for measuring the intensity of the interference light L4 and calculating portion 42 for carrying out balance detection of the detecting value of the photodetector 41a and the detecting value of the photodetector 41b. The interference light L4 is divided into two and detected in the photodetectors 41a and 41b.

The image obtaining means 50 detects the intensities of the reflected light beam L3 in positions in the direction of depth of the object S by carrying out Fourier-transform on the interference light L4 detected by the interference light detecting means 40 and obtains a tomographic image of the object S. The obtained tomographic image is displayed on a display means 60.

Here, detection of the interference light beam L4 in the interference light detecting means 40 and image generation in the image obtaining means 50 will be described briefly. Note that a detailed description of these two points can be found in M. Takeda, "Optical Frequency Scanning Interference Microscopes", Optical Engineering Contact, Vol. 41, No. 7, pp. 426-432, 2003.

When it is assumed that the light intensity of the interference fringes corresponding to each optical path length 1 when the reflected light beams L3 from depths of the object S and the reference light beam L2 interfere with each other with various optical path length differences is S(l), the light intensity I(k) detected in the interference light detecting means 40 is expressed by the following formula.

$$I(k) = \int_0^\infty S(l)[l + \cos(kl)] \, dl \qquad (1)$$

wherein k represents the wave number and l represents the optical path length difference. Formula (1) may be considered to be given as an interferogram of a frequency range having a wave number of ω/c (k=ω/c) as a variable. Accordingly, a tomographic image is obtained by obtaining in the image obtaining means 50 information on the distance of the object S from the measurement initiating position and information on the intensity of reflection by carrying out frequency analysis by Fourier-transform on the spectral interference fringes detected by the interference light detecting means 40 and determining the intensity S(l) of the interference light L4. The tomographic image is displayed by a display 60.

Operation of the optical tomography system 1 having a structure described above will be described with reference to FIGS. 1 and 2, hereinbelow. When a tomographic image is to be obtained, the optical path length is first adjusted by moving the movable stage 23 in the direction of the arrow A so that the object S is positioned in the measurable area. The laser beam L is subsequently emitted from the light source unit 10 by sweeping the wavelength at a period and the laser beam L is divided into the measuring light beam L1 and the reference light beam L2 by the dividing means 3. The measuring light beam L1 is led by the optical probe 30 into a body cavity and is projected onto the object S. Then the reflected light beam L3 from the object S and the reference light beam L2 reflected by the reflecting mirror 22 are multiplexed, and the interference light beam L4 of the reflected light beam L3 and the reference light beam L2 is detected by the interference light detecting means 40. A tomographic image is obtained by carrying out frequency analysis on a signal of the detected interference light beam L4 in the image obtaining means 50. In the optical tomography system 1 where a tomographic image is obtained by SS-OCT measurement, image information in the position in the direction of depth is obtained on the basis of the frequency and the intensity of the interference light beam L4, and the movement of the reflecting mirror 22 in the direction of arrow A is employed to adjust the measurement initiating position.

In the SS-OCT measurement described above, when the optical path length difference between the measuring light beam L1 and the reference light beam L2 becomes large, the quality of the image deteriorates due to increase in the spatial frequency, the relation of the sampling periods and/or the like. Accordingly, it is necessary to adjust the optical path length so that the optical path lengths of the measuring light beam L1 and the reference light beam L2 substantially conform to each other. The measurable range (measuring depth) is reverse proportional to a wavelength fluctuation width ΔΛ of the laser beam L, and the resolution when a tomographic image is obtained increases as the wavelength fluctuation width ΔΛ becomes larger. (See FIG. 2) That is, the measurable range becomes narrow when a tomographic image is obtained at a high resolution. Accordingly, it takes a large labor to bring the optical path length difference between the measuring light and the reference light to the measurable range since the measurable range (measuring depth) is narrow to obtain a tomographic image in order to adjust the measurement initiating position in an SS-OCT system for obtaining a high resolution tomographic image.

Accordingly, the optical tomography system 1 shown in FIG. 1 is provided with a control means 70 which switches between a measurement initiating position adjusting mode where a position for obtaining a tomographic image signal is adjusted in the direction of depth of the object S and an image obtaining mode where a tomographic image of the object S is obtained. The control means 70 controls the light source unit 10 or the interference light detecting means 40 so that the wavelength resolution of the interference light detecting means 40 is higher in the measurement initiating position adjusting mode than in the image obtaining mode.

That is, there are two ways to improve the wavelength resolution in detecting interference in the measurement initiating position adjusting mode. One is a method in which the wavelength resolution is increased by controlling the light source unit 10 so that the optical wavelength fluctuation width per unit time when the wavelength is swept is smaller in the measurement initiating position adjusting mode than in the image obtaining mode and the other is a method in which the wavelength resolution is increased by controlling the interference light detecting means 40 so that the sampling frequency is higher in the measurement initiating position adjusting mode than in the image obtaining mode. This point will be described in detail, hereinbelow.

Figure 3A:
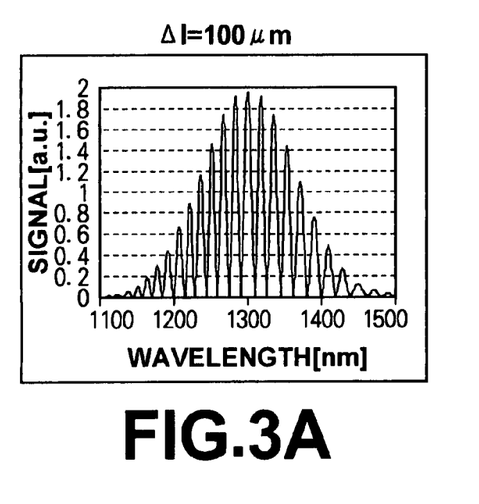
FIGS. 3A to 3C are views for illustrating an example of the interference light detected in the interference light detecting means shown in FIG. 1.
Figure 3B:
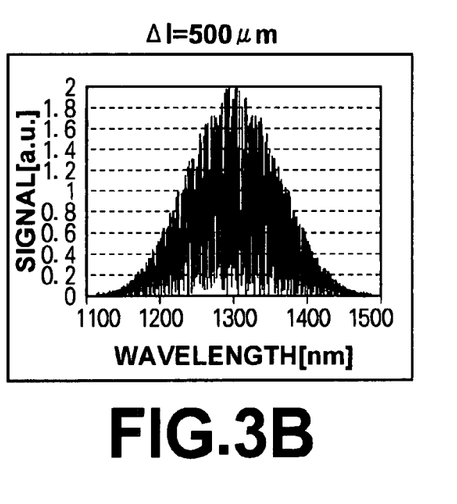
Figure 3C:
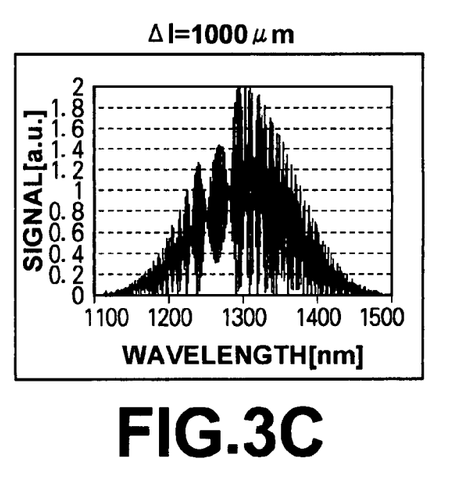
Figure 4:
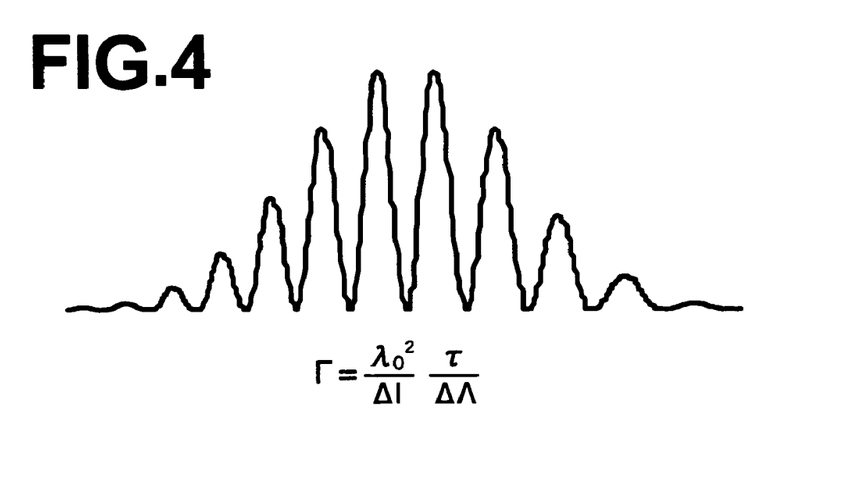
FIGS. 4 is a view for illustrating an example of the interference light detected in the interference light detecting means shown in FIG. 1.

Assuming that the optical path length difference Δl between the optical path length ls of the measuring light beam L1 and the optical path length lr of the reference light beam L2 is Δl=|lr−ls|, the period Γ of the interference light beam L4 detected by the interference light detecting means 40 such as shown in FIG. 4 is expressed by the following formula.

$$\Gamma = \lambda o^2 / \Delta l \cdot \tau / \Delta \Lambda \qquad (2)$$

wherein λo represents the central wavelength of the spectrum, τ represents the fluctuating period at which the wavelength fluctuates when the wavelength is swept and ΔΛ represents the wavelength fluctuation width (FIG. 2). FIGS. 3A, 3B and 3C respectively show the waveforms when Δl=100 μm, Δl=500 μm, Δl=1000 μm with the sampling frequency of 500/τ. As can be understood from FIGS. 3A, 3B and 3C and the formula (2), as the optical path length difference Δl increases, the period Γ of the interference light beam L4 becomes shorter.

In order to obtain a signal at a sufficient resolution, four or more than four samplings per one period of fluctuation is necessary as follows.

sampling periods Δt<Γ/4 of the interference light beam (3)

When formula (3) is not satisfied, the period Γ of the interference light beam L4 exceeds the resolution of the interference light detecting means 40 as shown in FIG. 3C and S/N deteriorates, which results in deterioration of the quality of the image.

The final measurable depth $\Delta l_{lim}$ of the object S is as follows from the formulae (2) and (3).

$$\Delta l_{lim} = 1/4 \cdot (\tau / \Delta \Lambda) \cdot \lambda o^2 \cdot (1/t) \qquad (4)$$

Formula (4) represents that the measurable depth $\Delta l_{lim}$ of the object S, that is, the measurable range (measuring depth), is reverse proportional to the inverse number of the wavelength fluctuation width (ΔΛ/τ) per unit time and proportional to the inverse number of the sampling interval Δt or the sampling frequency.

In the image obtaining mode, it is necessary to obtain a high quality image. For this purpose, it is preferred that the wavelength fluctuation width $\Delta\Lambda$ be large and the measuring resolution be high. Further, since it is necessary to obtain a tomographic image within a predetermined time, it is preferred that the wavelength sweeping period $\tau$ be short. Further, when the sampling frequency is large, the sampling time for one sampling becomes short, and when the amount of interference light detected by the interference light detecting means 40 is small, an amount of detected light is insufficient, which involves a fear that S/N deteriorates. Accordingly, it is not preferred that the sampling frequency is too large. Taking into account these conditions, the wavelength fluctuation width $\Delta\Lambda$, the wavelength sweeping period $\tau$, the sampling frequency and the like in the image obtaining mode are determined. Accordingly, the measurable range (measuring depth) where a tomographic image can be obtained is normally not so large. For example, when the measurable range is several tens of μm and the object is apart from the probe 30 by several hundreds of μm, the position of the object S cannot be realized even if a tomographic image is obtained.

Figure 5:
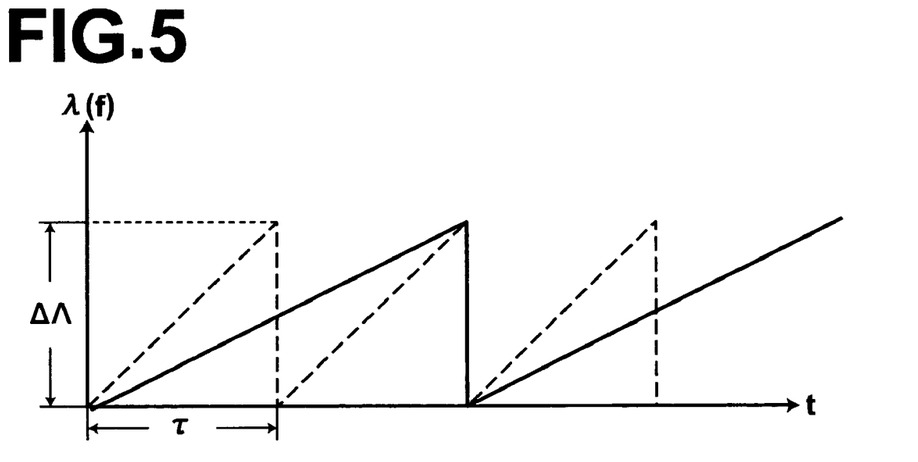
FIG. 5 is a view for illustrating an example of the wavelength fluctuation of a laser beam output from the light source unit shown in FIG. 1 in the measurement initiating position adjusting mode.

In this embodiment, the control means 70, for instance, reduces the rotational speed of the rotating polygon mirror 16 in the measurement initiating position adjusting mode to ½ of that in the image obtaining mode. With this arrangement, the wavelength sweeping period $\tau$ is doubled, and a laser beam L which is ½ in the wavelength fluctuation width ($\Delta\Lambda/\tau$) per unit time is emitted from the light source unit 10 as shown in FIG. 5. Thus when the wavelength fluctuation width ($\Delta\Lambda/\tau$) per unit time is reduced ($\tau/\Delta\Lambda$ is increased), the wavelength fluctuation width for one sampling in the interference light detecting means 40 is reduced that is, the apparent resolution in the interference light detecting means 40 is increased. In this embodiment, the measurable range $\Delta l_{lim}$ of the object S shown in formula (4) is doubled. By this, a tomographic image which is doubled in the measurable range (measuring depth) can be obtained and the object S comes to be easily imaged in the tomographic image. The user can carry out adjustment of the measurement initiating position simply at high speed observing the tomographic image.

In the case where the light source unit 10 is controlled so that the wavelength fluctuation width per unit time of the light when the wavelength is swept is smaller in the measurement initiating position adjusting mode than in the image obtaining mode to increase the resolution, though an obtaining time required to obtain one tomographic image is increased, there is no trouble in the normal tomographic image obtaining action since it is only when the measurement initiating position is adjusted.

Also when a wide measurable range (measuring depth) is required as when the layer structure of the stomach wall, for instance, a tomographic image which is wide in the measurable range (measuring depth) can be obtained by thus making smaller the wavelength fluctuation width per unit time.

Otherwise, the control means 70 may control the interference light detecting means 40 so that the sampling interval $\Delta t$ is smaller in the measurement initiating position adjusting mode than in the tomographic image obtaining mode or so that the sampling frequency ($1/\Delta t$) is larger in the measurement initiating position adjusting mode than in the tomographic image obtaining mode. That is, when the wavelength resolution in the interference light detecting means 40 is improved, the measurable range $\Delta l_{lim}$ is widened (see, fortmula 4) and a tomographic image which is wide in the measurable range (measuring depth) can be obtained. Accordingly, the object S comes to be easily imaged in the tomographic image and the user can carry out adjustment of the measurement initiating position simply at high speed observing the tomographic image. Though a sufficient amount of light cannot be obtained in the interference light detecting means 40, thereby involving deterioration of the image quality when the sampling frequency is high, the tomographic image may only have to be an image which has such a quality in which existence of the object can be recognized and does not require a high image quality in the measurement initiating position adjustment. When the sampling frequency ($1/\Delta t$) is increased, an obtaining time required to obtain one tomographic image is not increased and adjustment of the measurement initiating position can be carried out at high speed, Embodiments of the present invention are not limited to the embodiments described above. For example, though in the embodiment shown in FIG. 5, the wavelength period $\tau$ is increased, the wavelength fluctuation width $\Delta\Lambda$ may be narrowed. In this case, the light source unit 10 may be provided with a pair of rotating polygon mirrors different in diameter so that in the image obtaining mode, a rotating polygon mirror of a larger diameter is employed while in the measurement initiating position adjusting mode, the other mirror is employed. Further, the rotational speeds may be changed according to the mode described above.

Though a structure employing a rotating polygon mirror is shown in FIG. 1 as an example of the light source unit which emits a laser beam L while sweeping the wavelength thereof, a known wavelength-variable laser can be employed. In this case, the control means 70 controls the drive of the wavelength-variable laser so that $\Delta\Lambda/\tau$ is smaller in the measurement initiating position adjusting mode than in the image obtaining mode.

Further, though in the above embodiments, the light source unit 10 or the interference light detecting means 40 is controlled, both the light source unit 10 and the interference light detecting means 40 may be controlled. That is, it is possible to increase the sampling frequency in the interference light detecting means 40 while the wavelength fluctuation width per unit time in the light source unit 10 is narrowed.

What is claimed is:

1. An optical tomography system for obtaining a tomographic image of an object to be measured comprising
   a light source unit which emits light while sweeping the wavelength thereof at predetermined periods,
   a light dividing means which divides the light emitted from the light source unit into measuring light and reference light,
   a multiplexing means which multiplexes the reflected light from the object when the measuring light divided by the light dividing means is projected onto the object and the reference light,
   an interference light detecting means which detects interference light of the reflected light and the reference light which have been multiplexed by the multiplexing means, and
   a tomographic information obtaining means which obtains a tomographic information of the object by carrying out frequency-analysis on the interference light detected by the interference light detecting means,
   a detecting mode control means which switches between a first detecting mode in which the interference light is detected at a first wavelength resolution and a second detecting mode in which the interference light is detected at a second wavelength resolution higher than the first wavelength resolution being provided.

2. An optical tomography system as defined in claim 1 in which the light source unit comprises a light source where the fluctuation width of the wavelength per unit time of the light when the wavelength is swept can be switched, and
the detecting mode control means controls the light source unit so that the fluctuation width of the wavelength per unit time of the light when the wavelength is swept is smaller in the second detecting mode than in the first detecting mode.

3. An optical tomography system as defined in claim 2 in which the interference light detecting means detects the interference light by sampling the interference light at a predetermined sampling frequency, and
the detecting mode control means controls the interference light detecting means so that the sampling frequency is higher in the second detecting mode than in the first detecting mode.

4. An optical tomography system as defined in claim 1 in which the interference light detecting means detects the interference light by sampling the interference light at a predetermined sampling frequency, and
the detecting mode control means controls the interference light detecting means so that the sampling frequency is higher in the second detecting mode than in the first detecting mode.

5. An optical tomography system as defined in claim 1 in which the first detecting mode is an image obtaining mode for obtaining a tomographic image of the object and the second detecting mode is a measurement initiating position adjusting mode in which the position in the direction of depth of the object in which tomographic image signal is to be obtained is adjusted.

6. An optical tomography system as defined in claim 2 in which the first detecting mode is an image obtaining mode for obtaining a tomographic image of the object and the second detecting mode is a measurement initiating position adjusting mode in which the position in the direction of depth of the object in which tomographic image signal is to be obtained is adjusted.

7. An optical tomography system as defined in claim 3 in which the first detecting mode is an image obtaining mode for obtaining a tomographic image of the object and the second detecting mode is a measurement initiating position adjusting mode in which the position in the direction of depth of the object in which tomographic image signal is to be obtained is adjusted.

8. An optical tomography system as defined in claim 4 in which the first detecting mode is an image obtaining mode for obtaining a tomographic image of the object and the second detecting mode is a measurement initiating position adjusting mode in which the position in the direction of depth of the object in which tomographic image signal is to be obtained is adjusted.

9. An optical tomography system as defined in claim 1 further comprising an optical path length adjusting means which adjusts the optical path length of the measuring light or the reference light.

10. An optical tomography system as defined in claim 2 further comprising an optical path length adjusting means which adjusts the optical path length of the measuring light or the reference light.

11. An optical tomography system as defined in claim 3 further comprising an optical path length adjusting means which adjusts the optical path length of the measuring light or the reference light.

12. An optical tomography system as defined in claim 4 further comprising an optical path length adjusting means which adjusts the optical path length of the measuring light or the reference light.

13. An optical tomography system as defined in claim 5 further comprising an optical path length adjusting means which adjusts the optical path length of the measuring light or the reference light.

14. An optical tomography system as defined in claim 6 further comprising an optical path length adjusting means which adjusts the optical path length of the measuring light or the reference light.

15. An optical tomography system as defined in claim 7 further comprising an optical path length adjusting means which adjusts the optical path length of the measuring light or the reference light.

16. An optical tomography system as defined in claim 8 further comprising an optical path length adjusting means which adjusts the optical path length of the measuring light or the reference light.

17. An optical tomography system as defined in claim 9 further comprising an optical path length adjusting means which adjusts the optical path length of the measuring light or the reference light.

* * * * *